United States Patent
Landry et al.

(10) Patent No.: US 10,531,897 B2
(45) Date of Patent: Jan. 14, 2020

(54) IMPLANTABLE DEVICE FOR RELIEVING ANKLE PAIN

(75) Inventors: Michael E. Landry, Austin, TX (US);
Stefan Gabriel, Mattapoisett, MA (US);
Anton G. Clifford, Mountain View, CA (US); David Lowe, Redwood City, CA (US)

(73) Assignee: MOXIMED, INC., Fremont, CA (US)

( * ) Notice: Subject to any disclaimer, the term of this patent is extended or adjusted under 35 U.S.C. 154(b) by 75 days.

(21) Appl. No.: 13/218,270

(22) Filed: Aug. 25, 2011

(65) Prior Publication Data

US 2012/0053644 A1   Mar. 1, 2012

Related U.S. Application Data

(60) Provisional application No. 61/377,217, filed on Aug. 26, 2010.

(51) Int. Cl.
*A61B 17/68* (2006.01)

(52) U.S. Cl.
CPC .................................. *A61B 17/68* (2013.01)

(58) Field of Classification Search
CPC ...... A61F 2/4202; A61F 2/4261; A61B 17/70; A61B 17/7014; A61B 17/7019; A61B 17/7023; A61B 17/7025; A61B 17/7028; A61B 2017/567; A61B 2017/681
USPC ...... 606/86 R, 88, 105, 246–278; 623/21.18, 623/13.12–13.14
See application file for complete search history.

(56) References Cited

U.S. PATENT DOCUMENTS

| | | | |
|---|---|---|---|
| 8,328,962 B2* | 12/2012 | Schussler | 148/402 |
| 2006/0036240 A1* | 2/2006 | Colleran et al. | 606/61 |
| 2006/0189985 A1* | 8/2006 | Lewis | A61B 17/7007 606/257 |
| 2006/0264941 A1* | 11/2006 | Lins | A61B 17/7059 606/257 |
| 2008/0275552 A1* | 11/2008 | Makower et al. | 623/13.13 |
| 2008/0275555 A1* | 11/2008 | Makower et al. | 623/14.12 |

FOREIGN PATENT DOCUMENTS

WO   WO2009155542   12/2009

* cited by examiner

*Primary Examiner* — Si Ming Ku
(74) *Attorney, Agent, or Firm* — Cermak Nakajima & McGowan LLP; Malcolm K. McGowan

(57) ABSTRACT

An apparatus and related method for controlling a load on a human ankle joint during normal gait while preserving motion. The approach is intended to treat osteoarthritis and pain of the ankle without substantially resisting an angular displacement associated with full mobility of the ankle joint. In one particular embodiment, the device includes a first load transmission support, a second load transmission support and an implantable compressible absorber.

19 Claims, 7 Drawing Sheets

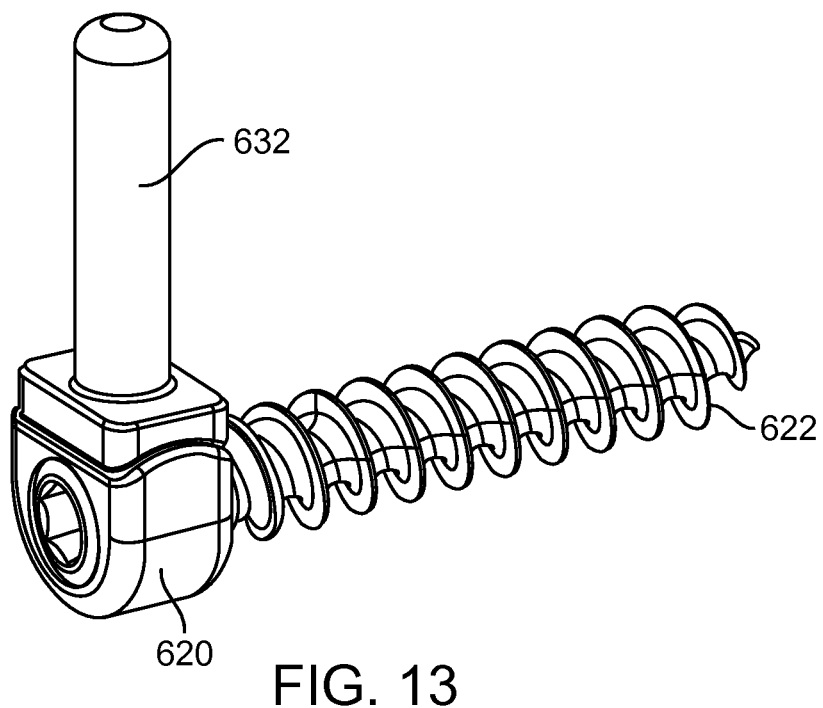
FIG. 13
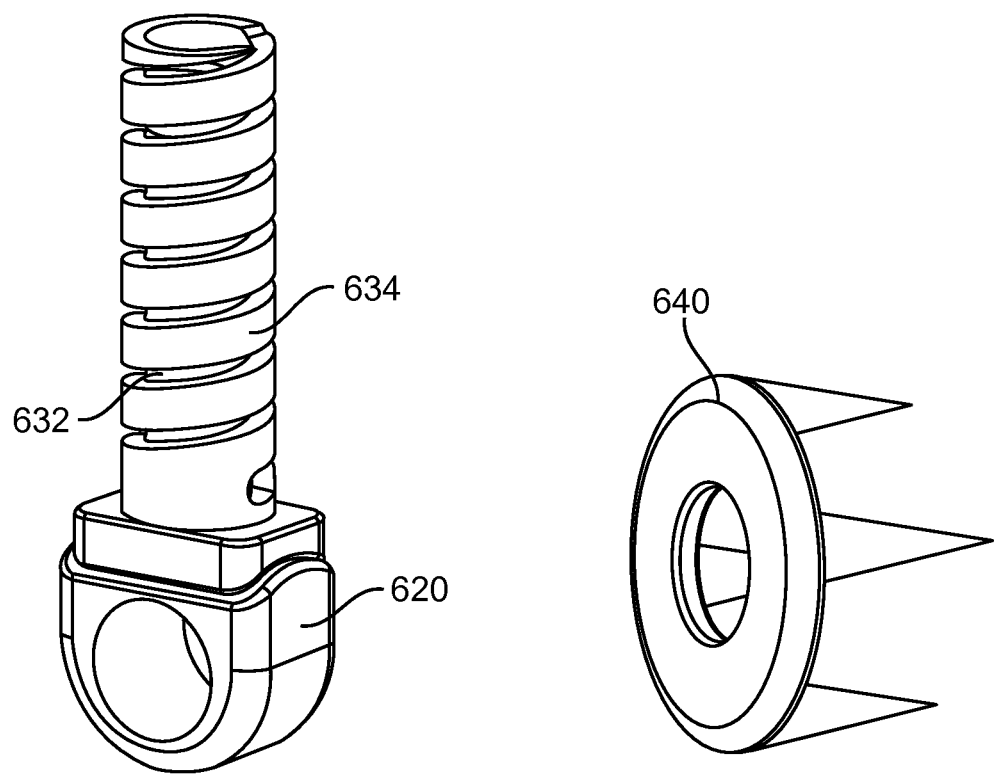
FIG. 14
FIG. 15 ically designed to absorb shocks and distribute the load
IMPLANTABLE DEVICE FOR RELIEVING ANKLE PAIN

BACKGROUND OF THE INVENTION

The present disclosure is directed toward apparatus and methods for treating joints and in particular, to treating ankle joints affected with osteoarthritis.

A joint is the location at which two or more bones make contact. Joints are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. In fibrous/immovable joints, bones are connected by dense connective tissue, consisting mainly of collagen. The fibrous joints are further divided into three types:
- sutures which are found between bones of the skull;
- syndesmosis which are found between long bones of the body; and
- gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Cartilaginous joints include the artificial discs of the spine.

Synovial joints have a space between the articulating bones and surrounding cartilage for synovial fluid. This classification contains joints that are the most mobile of the three, and includes the hip, knee, ankle and shoulder.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Diarthrosis joints permit a variety of movements (e.g. flexion, adduction, pronation). Only synovial joints are diarthrodial and they can be divided into six classes according to their motion: 1. ball and socket—such as the shoulder or the hip; 2. hinge—such as the elbow and ankle; 3. pivot—such as the radius and ulna; 4. condyloidal (or ellipsoidal)—such as the wrist between radius and carps or knee; 5. saddle—such as the thumb joint; and 6. gliding—such as between the carpals.

Synovial joints (or diarthrosis or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

A particular form of OA is post-traumatic osteoarthritis or PTOA. As it is understood, articular surface incongruities resulting from trauma are believed to subject a joint to elevated contact stresses which over time results in the development of PTOA in the joint. Finite element stress analysis has been employed to assess joint mechanics throughout an entire sequence of load variation encountered during gait (See "Is Elevated Contact Stress Predictive of Post-Traumatic Osteoarthritis for imprecisely Reduced Tibial Plafond Fractures?," Anderson et al., 2010 Orthopaedic Research Society, Wiley Periodicals, Inc.). While recognizing that joint loading is intermittent and varies over a gait cycle, FE modeling techniques have enabled the computation of elevated contact stresses produced by incongruities from trauma such as a fracture. It has thus been possible to assess a relationship between elevated contact stresses and PTOA onset in joints of patients with intra-articular fractures by comparing stresses within joints suffering from trauma to stresses within intact joints.

The main symptom of osteoarthritis is chronic pain, causing loss of mobility and often stiffness. "Pain" is generally described as a sharp ache, or a burning sensation in the associated muscles and tendons. OA can cause a crackling noise (called "crepitus") when the affected joint is moved or touched, and patients may experience muscle spasm and contractions in the tendons. Occasionally, the joints may also be filled with fluid. Humid weather increases the pain in many patients.

OA affects the hand, feet, spine, and the large weight-bearing joints, such as the hips, knees and ankles, although in theory, any joint in the body can be affected. OA may begin or progress if excess stress or weight is placed on the joint. Several conditions can lead to excess stress or weight on the joint, including anatomy, injury, or obesity. When too much stress is placed on the joint as OA progresses, the affected joint appears larger, is stiff and painful, and usually feels worse, the more the joint is used and loaded throughout the day, thus distinguishing OA from rheumatoid arthritis. With progression in OA, cartilage looses its viscoelastic properties and its ability to absorb load. Generally speaking, the process of clinical detectable osteoarthritis is irreversible, and typical treatment consists of medication or other interventions that can reduce the pain of OA and thereby improve the function of the joint. While drugs and certain cartilage repair procedures may temporarily relieve pain, they often do not treat the underlying problems that led to OA. Conversely, research suggests that if the excess stress on the joint is removed, pain may decrease, and the natural joint tissues may demonstrate some recovery.

A variety of surgical procedures have been developed with the aim of decreasing or eliminating pain and improving function in patients with advanced osteoarthritis (OA). The different approaches include preservation or restoration of articular surfaces, total joint replacement with artificial implants, osteotomy and arthrodesis (fusion).

Arthrodesis are described as being reasonable alternatives for treating OA of small hand and foot joints as well as degenerative disorders of the spine, but were deemed to be rarely indicated in large weight-bearing joints such as the hip due to functional impairment of gait, cosmetic problems and further side-effects. Arthrodesis of the ankle is used as a last resort procedure and is often successful in relieving pain, however, gait and mobility are adversely affected.

Joint replacement is one of the most common and successful operations in modern orthopaedic surgery. It consists of replacing painful, arthritic, worn or diseased parts of the joint with artificial surfaces shaped in such a way as to allow joint movement. Such procedures are a last resort treatment as they are highly invasive and require substantial periods of recovery. Joint replacement is sometimes called total joint replacement indicating that all joint surfaces are replaced. This contrasts with hemiarthroplasty (half arthroplasty) in which only one bone's joint surface is replaced and unincompartmental arthroplasty in which both surfaces of the knee, for example, are replaced but only on the inner or outer sides, not both. Thus, arthroplasty as a general term, is an operative procedure of orthopaedic surgery performed, in which the arthritic or dysfunctional joint surface is replaced. Alternatively, loading patterns and associated stresses on painful joints can be modified by realigning the joint by osteotomy or other procedures. These procedures are all characterized by relatively long recovery times and are highly invasive procedures.

Other approaches to treating osteoarthritis involve an analysis of loads which exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. Research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as unloader braces or fixators which control the motion of the bones at a joint. Various of these approaches have had some success in alleviating pain but suffer from lack of patient compliance or lack an ability to facilitate and support the natural motion and function of the diseased joint.

In osteoarthritis of the ankle the cartilage that normally allows the ankle to move smoothly has broken down. When the gliding surface of the cartilage is damaged, the lower ends of the tibia and fibula grind against the top of the talus, creating pain and loss of normal ankle movement. Osteoarthritis can occur in patients due to genetic predisposition and ordinary wear and tear or can be associated with trauma. As stated, trauma related arthritis results when the joint is injured either by fracture, dislocation or damage to the ligaments surrounding the joint. This resulting damage predisposes the joint to osteoarthritis.

Treatments for ankle osteoarthritis include conservative approaches such as weight loss, physical therapy and anti-inflammatory medicine. However, clinical literature correlating and quantifying OA relief from weight loss has not been identified with respect to the ankle. In more severe cases, surgical interventions including distal tibial osteotomy, ankle replacement or fusion may be required. Ankle replacement is a form of joint replacement where the ankle joints are replaced with artificial joints made from metal alloys and lightweight plastic. Ankle fusion is the other option where the bones of the ankle joint are locked together with screws and plates. Ankle fusion and replacement procedures are characterized by relatively long recovery times and are highly invasive procedures.

There is a need for a treatment modality which bridges the gap between the more conservative approaches such as weight loss, physical therapy and anti-inflammatory medicine and a decision to seek major surgical intervention. Such a treatment modality should be minimally invasive yet sufficiently effective to reduce the pain of osteoarthritis. The treatment should also be compatible with ankle anatomy taking into consideration the tendons and muscles overlaying the ankle joint and relatively thin skin at the ankle, as well as contact stresses within the joint. In particular, consideration of measured contact stresses and a predetermined threshold can be useful in directing treatment. The treatment should not be hindering or only minimally hinder normal motion of the ankle joint.

The present disclosure addresses these and other needs.

SUMMARY

Briefly and in general terms, the present disclosure is directed towards apparatus and methods for treating the ankle. Various structures are presented to treat ankle pain and more specifically to treat pain associated with osteoarthritis of the ankle joint.

In one aspect, there is disclosed an implantable load absorbing device for reducing ankle pain, the device includes a first load transmission support configured to be secured to a medial side of the tibia and a second load transmission support configured to be secured to a medial side of the talus. An implantable compressible absorber is secured to the first support and the second support. The absorber is configured to off load at least a portion of a compressive load normally experienced by the natural ankle joint.

In another aspect, there is disclosed an implantable device for reducing ankle pain including a first load transmission support configured to be secured to the tibia or fibula and a second load transmission support configured to be secured to the talus. An implantable absorber is positioned between the first support and the second support and has at least a first degree of rotational freedom of motion and a first degree of translational freedom of movement to allow ankle motion while absorbing at least a portion of a compressive load normally experienced by the natural ankle joint.

In a further aspect, there is disclosed an implantable device for reducing ankle pain including a first load transmission support configured to be secured to the tibia or fibula and a second load transmission support configured to be secured to a the talus such that the second support is in contact with the first support during a portion of the natural motion of the ankle joint. At least one spring element is provided in the first or second support to absorb at least a portion of a compressive load normally experienced by the natural ankle joint.

A method of treating a joint is also disclosed. In one approach, the method involves employing an implantable load absorbing device to maintain contact stress between bones defining a joint below a predetermined threshold. In a specific method of treating a joint in general or one suffering from trauma, contact stresses are measured, a determination is made whether the measured contact stresses exceed a predetermined threshold, and a load absorbing device is implanted if contact stresses exceed a threshold.

In another specific application, incongruities in joint surfaces are identified and a correlation is made to identify increases in joint stresses resulting from such incongruities (e.g. fractures) which may lead to the onset of post traumatic OA (PTOA). Taking time intervals for ankle loading and a reasonable walking cadence into consideration, as well as the percentage of gait cycle which is in stance, a target pressure reduction per gait cycle for pain relief is estimated. In one embodiment, a force reduction of 20-40 pounds is contemplated.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIG. 13 is perspective view of the talus load transmission support, absorber piston and talus screw of the device of FIG. 10;

FIG. 14 is a perspective view of the talus load transmission support, absorber piston and absorber spring of the device of FIG. 10; and FIG. 15 is a perspective view of the force distributing washer of the device of FIG. 10.

DETAILED DESCRIPTION OF THE PREFERRED EMBODIMENTS

Figure 1:
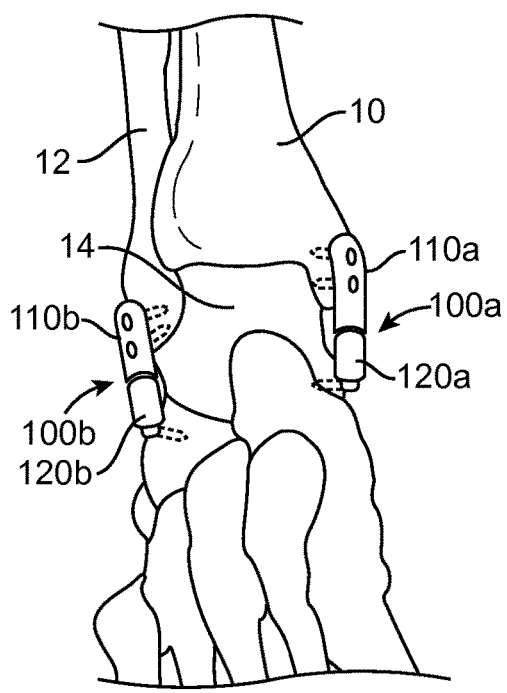
FIG. 1 is a front view, depicting an ankle joint and a pair of implantable devices for reliving ankle pain.

Referring now to the drawings, which are provided by way of example and not limitation, the present invention is directed towards apparatus and methods for treating the ankle joint. The present disclosure seeks to alleviate pain associated with the function of osteoarthritis of the ankle joint and other pain in the ankle joint. Whereas the present disclosure is particularly suited to address issues associated with osteoarthritis of a hinged synovial joint, the energy manipulation accomplished by the disclosed apparatus and methods lends itself well to broader applications.

The implantable devices shown and described herein are connected across a joint, such as an ankle joint, for reducing pain in the joint by reducing joint loading. The implantable load absorbing devices generally include a first load transmission support configured to be secured to the tibia and a second load transmission support configured to be secured to the talus on the medial and/or lateral side of the ankle joint. An implantable compressible absorber positioned between the first load transmission support and the second load transmission support absorbs at least a portion of a compressive load normally experienced by the natural ankle joint. The implantable device is configured to allow natural or near natural ankle motion in the joint.

Figure 2:
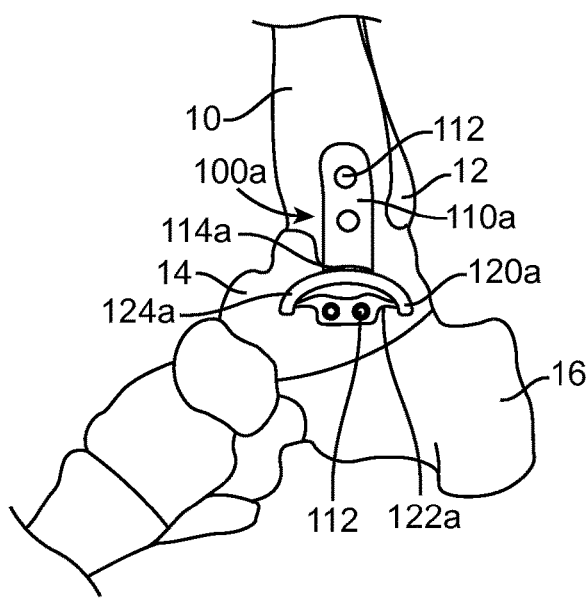
FIG. 2 is a medial side view of the ankle and implantable device of FIG. 1.
Figure 3:
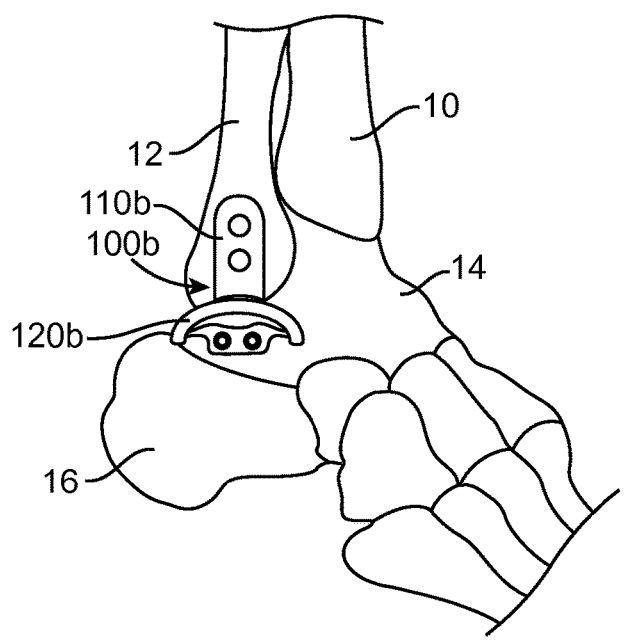
FIG. 3 is a lateral side view of the ankle and implantable device of FIG. 1.

As background, the ankle joint is made up of three bones which are movable with respect to one another, as shown in FIGS. 1-3. The bones include the lower end of the tibia 10, the lower end of the fibula 12 which together form a mortise shaped socket and the talus 14 which fits into the socket formed by the tibia and the fibula. The talus sits on top of the calcaneus 16 or heel bone. The ankle joint works like a hinge to allow your foot to move up (dorsiflexion) and down (plantarflexion).

There are ligaments on both sides of the ankle joint that hold the bones together. There are many tendons that cross the ankle to move the ankle and move the toes. Ligaments connect bones to bones while tendons connect muscles to bones. The large Achilles tendon in the back of the ankle is the most powerful tendon in the foot. It connects the calf muscles to the heel bone and gives the foot the power to walk, run and jump. Inside the joint, the bones are covered with articular cartilage. Articular cartilage is the material that allows the bones to move against one another in the joints of the body. The cartilage lining varies in thickness between joints and within each joint.

Range of motion of an ankle joint between the tibia, the fibula and the talus is described in terms of functional range of motion (FROM), such as when walking and maximum range of motion (MROM). The MROM includes plantarflexion (movement downward) 0-40 degrees; dorsiflexion (movement upward) 0-20 degrees; foot inversion (turned inward) 0-18; foot eversion (turned outward) 0-8 degrees; external rotation 0-12 degrees; and internal rotation 0-15 degrees. The FROM includes plantarflexion 0-10 degrees; dorsiflexion 0-15 degrees; foot inversion (turned inward) 0-5; foot eversion (turned outward) 0-5 degrees; external rotation 0-5 degrees; and internal rotation 0-5 degrees.

FIGS. 1-3 illustrate an ankle joint with implantable load absorbing devices 100a, 100b implanted on each side of the ankle joint in order to provide load bypassing support for the ankle joint. The devices 100a, 100b are implanted outside of the ankle joint capsule and beneath the skin. This extracapsular, subcutaneous implant provides a joint preserving technology, uniquely designed to allow the implant to be removed for future treatments such as a joint replacement. The implantable devices 100a, 100b may be used either alone or together to treat OA pain by absorbing excess weight placed on the ankle joint. By reducing the weight supported by the diseased ankle, the load absorbing system is intended to protect cartilage while maintaining the joint's natural motion and structural integrity. The load absorbing devices 110a, 100b of FIGS. 1-3 and the other load absorbing devices described herein are designed to create a slender device profile which avoids impinging on the tissues surrounding the joint.

The load absorbing devices 100a, 100b also permit and complement the unique articulating motion of the ankle joint of a patient while simultaneously reducing load being experienced by both cartilage and osseous tissue (cancellous and cortical bone) of the ankle joint. The devices described herein involve varying amounts and locations of energy absorption and transfer from the ankle joint to the implanted device positioned alongside the joint. Depending on the geometry selected for the load absorbing devices 100a, 100b, the amount of energy absorption during the pivoting of the ankle joint may be selected to vary during different phases of the gait cycle. When the load absorbing devices 100a, 100b are implanted at an ankle joint, some of the load normally transferred through the ankle joint is transferred through the device instead of through the ankle. The device absorbs energy in a spring or other energy absorber when the ankle is loaded and the energy is temporarily stored in the absorber. The energy is returned when the joint is unloaded. This transfer of load can also be described as off loading of the loads on the natural ankle joint.

The implantable load absorbing device 100a, as shown in FIG. 2, includes a tibial load transmission support 110a fixed to the tibia 10 by bone screws 112 or other fixation devices and a talus load transmission support 120a fixed to the talus 14 by additional bone screws 112. The talus support 120a is formed as a combination of a rail 124a and absorber 122a. The absorber 122a includes a flexible leaf spring element which is shown in the compressed (load absorbing or active) configuration in FIG. 2. For an illustration of an uncompressed (passive) configuration in a different device, see the embodiment of FIGS. 5 and 6. The tibial support 110a has a lower end formed as a follower 114a which remains in contact with and travels along the rail 124a of the talus support 120a. The spring element 122a may be secured to the rail 124a in movable manner, such as positioned in a track or may be fixed.

A shape or contour of the rail 124a in the anterior posterior direction is determined based on a desired load absorption pattern for the ankle throughout the range of motion. For example, when maximum load absorption is needed during stance, a center portion of the rail can protrude to provide maximum load absorption (or distraction) to the joint space during this portion of the range of motion. When more load absorption is needed during flexion than extension, the anterior portion of the rail 124a drops downward more gradually than the posterior end of the rail. In this way the contour of the rail 124a can be designed to provide unloading to the ankle joint during the high load portions of the gait cycle while allowing the implant to be passive or nearly passive at low load portions of the gait. The rail 124a shape may be predetermined in a one size fits most design, may be provided in a series of shapes for customization or may be custom designed for each patient.

The cross sectional shape of the rail 124a and the cross sectional shape of the lower end of the follower 114a should match one another to form a low wear bearing surface. In one example, the rail 124a can be convex and the follower 114a concave to match and track along the rail. In addition, the materials selected for these bearing surfaces should be low wear combinations.

The materials for parts of the implants can include metals, such as titanium, titanium alloy or cobalt chromium alloy; ceramic; high strength plastic such as polyetheretherketone (PEEK) or other durable materials. Combinations of materials can also be used to maximize the properties of materials for different parts of the device. At the wear surfaces, the material may include a combination of metal-on-poly, metal-on-metal, metal-on-ceramic or other combinations to minimize wear.

The absorber of the implant shown in FIGS. 1-3 uses the leaf spring 122a to provide absorption of a portion of the forces normally applied to the joint. It should be understood that the leaf spring may be replaced by one or more springs including coil springs, cantilever springs, torsion springs or flat springs. Alternatively, the absorber can use a non-spring energy absorbing element such as a hydraulic, pneumatic or magnetic energy absorbing element.

As shown in FIG. 2, the tibial and talus load transmission supports 110a, 120a are designed to fit on the tibia and talus at a location outside of the synovial joint space and to not interfere with the articulation of the ankle joint. On the medial side, the tibial support 110a is shown positioned on the medial malleolus (downward protruding part on the medial side of the tibia) by two locking bone screws 112. The talus support 120a is shown positioned on the medial side of the talus, just below the bottom of the medial malleolus and attached by two locking bone screws. Other attachment points and screw types are also contemplated.

As shown in FIG. 3, the lateral load absorbing device 100b is positioned on the lateral side of the ankle joint and is similar in design to the medial device 100a, but shaped and sized for the lateral location. On the lateral side, fibula and talus load transmission supports 110b, 120b are designed to fit on the fibula and talus at a location outside of the synovial joint space and to not interfere with the articulation of the ankle joint. As an alternative placement for the lateral device, the upper load transmission support 110b can be placed on the tibia just anterior of the fibula. The shapes of the support members 110a, 110b, 120a, 120b and types, placements and angulations of bone screws can be modified to accommodate for different placements and load transmission properties desired.

Whether one implantable load absorbing device or two devices (medial and lateral) are used on the ankle joint of a patient, the total of all the springs should off load at least 5% and up to 50% of the patient's total body weight to effect partial unloading of the ankle joint. In one example, the total of the springs on one ankle are designed to off load 10 to 60 pounds, preferably 30 to 50 pounds.

When customization of rail shape, support shape, or spring force is desired, such customization may be performed with the assistance of computer modeling of the joint from images of the joint.

Figure 4:
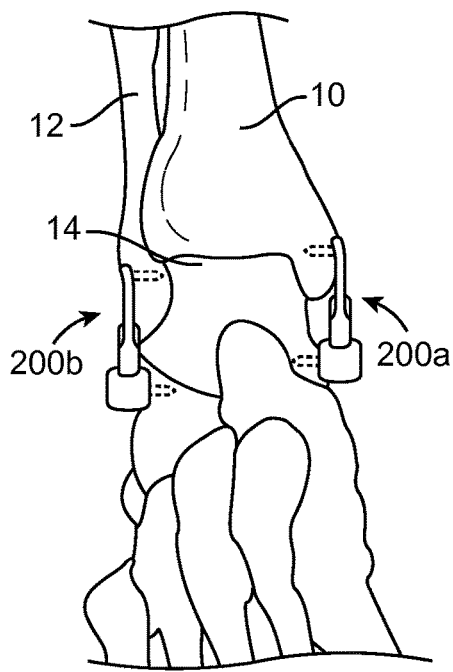
FIG. 4 is a front view, depicting an ankle joint and another pair of implantable devices for reliving ankle pain.
Figure 5:
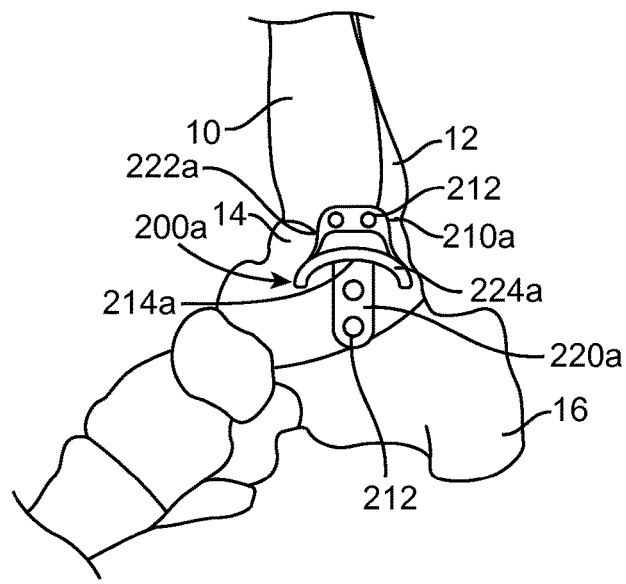
FIG. 5 is a medial side view of the ankle and implantable device of FIG. 4.
Figure 6:
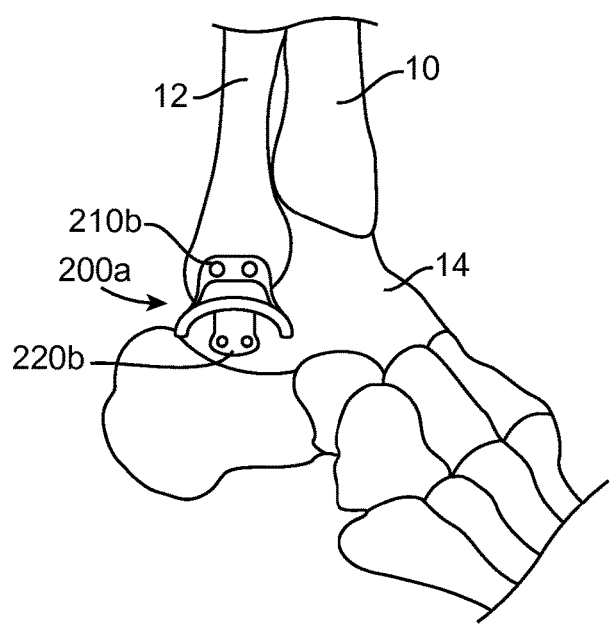
FIG. 6 is a lateral side view of the ankle and implantable device of FIG. 4.

FIGS. 4-6 show an ankle joint with an alternative embodiment of rail based implantable load absorbing devices 200a, 200b implanted on each side of the ankle joint in order to provide load bypassing support for the ankle joint. As in the embodiment of FIG. 1, the devices 200a, 200b are implanted outside of the ankle joint capsule and beneath the skin.

The medial side implantable load absorbing device 200a, as shown in FIG. 5, includes a tibial load transmission support 210a fixed to the tibia 10 by bone screws 212 or other fixation devices and a talus load transmission support 220a fixed to the talus 14 by additional bone screws 212. The tibial support 210a is formed as a combination of a rail 224a and absorber 222a. The absorber 222a includes a flexible leaf spring element which is shown in the uncompressed or passive configuration in FIG. 5. The leaf spring element may take on a variety of shapes including the U-shaped configuration shown. The talus support 220a has an upper end formed as a follower 214a which remains in contact with and travels along the rail 224a of the tibial support 210a. A shape or contour of the rail 224a can be varied based on a desired load absorption pattern for the ankle throughout the range of motion. The cross sectional shape of the rail 224a and the cross sectional shape of the upper end of the follower 214a should match one another to form a low wear bearing surface.

The lateral load absorbing device 200b is positioned on the lateral side of the ankle joint and is similar in design to the medial device 200a, but shaped and sized for the lateral location. On the lateral side, fibula and talus load transmission supports 210b, 220b are designed to fit on the fibula and talus at a location outside of the synovial joint space and to not interfere with the articulation of the ankle joint. Although FIGS. 1-6 illustrate embodiments with both medial and lateral rails positioned superiorly and followers positioned inferiorly, and the reversed, it is also contemplated that the medial and lateral sides may include load absorbing devices of different designs. For example, the medial load absorbing device 100a of FIG. 2 may be combined with the lateral load absorbing device 200b of FIG. 6.

Figure 7:
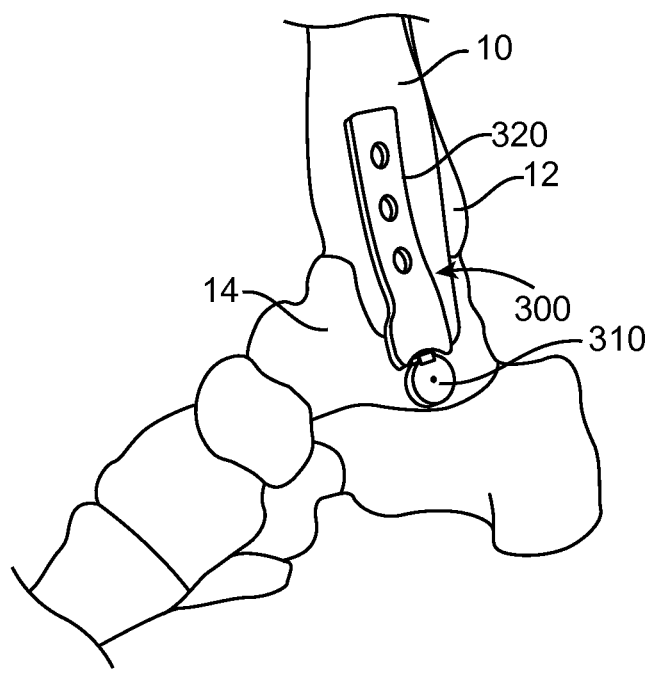
FIG. 7 is medial side view of an ankle joint and an implantable device for reliving ankle pain having a rod extending through the talus bone of the ankle.
Figure 8:
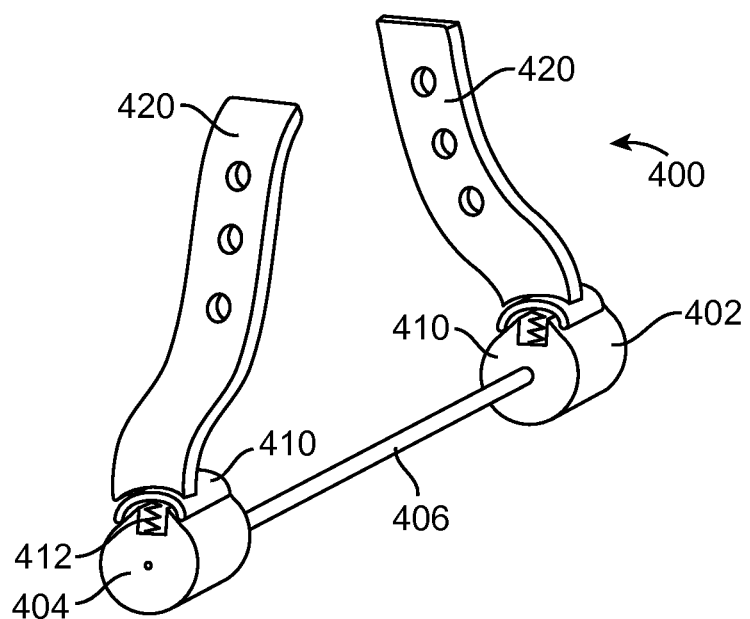
FIG. 8 is a perspective view of the implantable device of FIG. 7 removed from the ankle.

FIGS. 7 and 8 illustrate schematic views of a further embodiment of a unilateral or bilateral load absorbing device 300, 400 with a spring loaded cam. The load absorbing device 300 includes a cam element 310 fixed to the talus 14 and a superior load transmission support 320 fixed to either the tibia 10 or the fibula 12. An absorber element may be positioned within the cam element 310 and allow the upper bearing surface of the cam element to move up and down absorbing load as will be described in more detail with reference to FIG. 8 below. Alternatively, the absorber element can be provided within the superior load transmission support 320. The shape of the cam can be designed to reduce load on the ankle joint during a predetermined portion of the gait cycle, over the entire gait cycle, or over the entire range of motion of the joint. In one example, the load absorbing device provides unloading from 10 degrees plantarflexion (downward) to 15 degrees dorsiflexion (upward) of the ankle which would reduce loading during the entire gait cycle for the ankle. In another embodiment, the active unloading of the ankle is provided from ±5 degrees flexion to target more specific portions of the gait cycle, such as the peak loading portions of the gait cycle.

The load absorbing device 300 can allow a normal range of motion of an ankle joint in plantarflexion and dorsiflexion with the device providing unlimited motion in plantarflexion and dorsiflexion as the device allows free rotation of the superior support 320 about the cam 310. The device 300, as shown in FIG. 7 on the medial ankle, can allow normal range of foot eversion of about ±8 degrees by allowing the superior support 320 to lift off the cam 310. In the embodiment of FIG. 7, normal range of foot inversion of about 0-15 degrees may be limited somewhat, but some inversion is available due to the compression of the absorber. Some amount of limited internal and external rotation can also be allowed.

FIG. 8 illustrates an embodiment of a system 400 in which a lateral load absorbing device 402 is connected with a medial load absorbing device 404 by a shaft extending through the talus 14. FIG. 8 shows schematically spring elements 412 inside the cams 410. One or more spring elements 412 can be provided within each of the cams 410 to apply an unloading force to an upper bearing surface of the cams and the associated lower bearing surface of the superior supports 320. The superior supports 320 may be fixed both to the tibia 10 or medially to the tibia and laterally to the fibia 12. The supports 320 can be entirely outside of the bone or some bone may be resected for placement of the supports. Similarly, the cams 410 may be entirely outside the bone or partly recessed into the bone for a product which has less change to the natural contours of the bone.

The positioning of the shaft 406 and thus, the position of the cams will have a significant effect on the unloading provided by the load absorbing system 400. When the shaft 406 is positioned with the bearing surface of the cams 410 at a center of rotation of the ankle joint, the unloading will be provided substantially throughout motion of the ankle joint. When the bearing surfaces of the cams 410 are positioned above the joint center of rotation, unloading will occur only for a portion of the ankle range of motion. With a particular range of motion for unloading being able to be tailored by accurate positioning of the shaft 406.

The load absorbing systems 300, 400 allow one rotational degree of freedom by the rotational motion of the superior support 320, 420 over the cam 310, 410 and allow one translational degree of freedom by relative motion of the support and the cam in a direction parallel to the shaft 406. Additional degrees of freedom are provided due to the unlinked design of the devices 300, 400 which allow the parts to disengage with each other for additional motion of the ankle joint.

Figure 9:
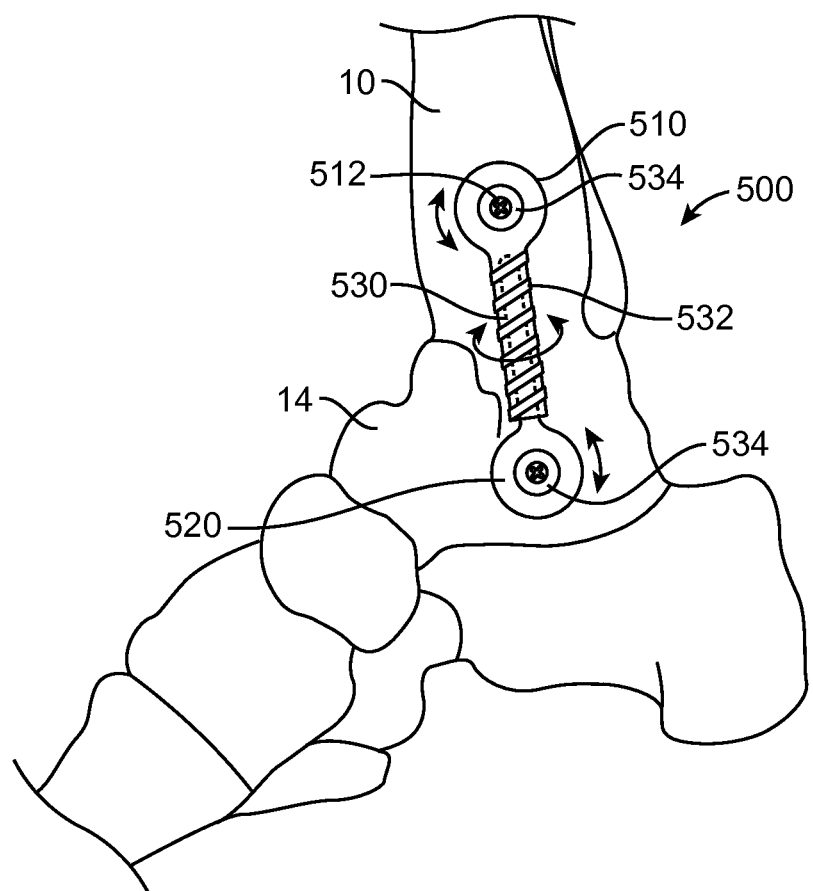
FIG. 9 is a medial side view of an ankle joint and a further implantable device for reliving ankle pain.
Figure 9A:
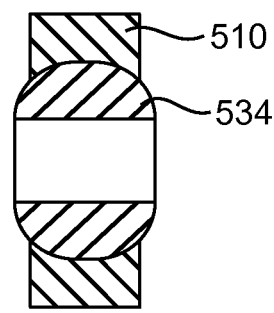
FIG. 9A is a cross sectional view of a portion of the spherical bearing of the device of FIG. 9.

FIG. 9 shows a further alternative implantable load absorbing device 500 located on the medial side of the ankle joint. The device includes a tibial support member 510, a talus support member 520 and an absorber 530 therebetween. The absorber 530 includes a central piston formed as a part of the talus support member 520. The piston is surrounded by a coaxial piston sleeve which forms a part of the tibial support member 510. An absorber spring 532 is located coaxially with the piston and sleeve and acts in compression to off load the ankle joint. As shown in the cross section of FIG. 9A, both the tibial and talus support members 510, 520 are connected to the bone via bearing members 534 in a ball and socket arrangement. The bearing members 534 allow the absorber to rotate with respect to the bones to which it is attached and may be secured to the bone by bone screws 512 with or without one or more washers. The load absorbing devices 500 allows a full range of motion in plantarflexion and dorsiflexion and a somewhat more limited range of motion in internal rotation, external rotation, inversion and eversion.

FIGS. 10-15 illustrate an implantable load absorbing device 600 for the medial side of the ankle joint which provides a slender profile by its location partially within a tunnel formed in the medial side of the tibia 10. The load absorbing device 600 includes a tibial support member 610, a talus support member 620 and an absorber 630 positioned therebetween. The compressible absorber 630 is configured to allow ankle motion while absorbing at least a portion of a compressive load normally experienced by the natural ankle joint. In the embodiment shown, the tibial support member 620 is fixed to the tibia with two tibial locking screws 612 while the talus support member 620 is secured to the talus by a talus screw 622. The talus screw 622 allows the talus support 620 to move longitudinally with respect to the screw as will be described in detail below.

Figure 10:
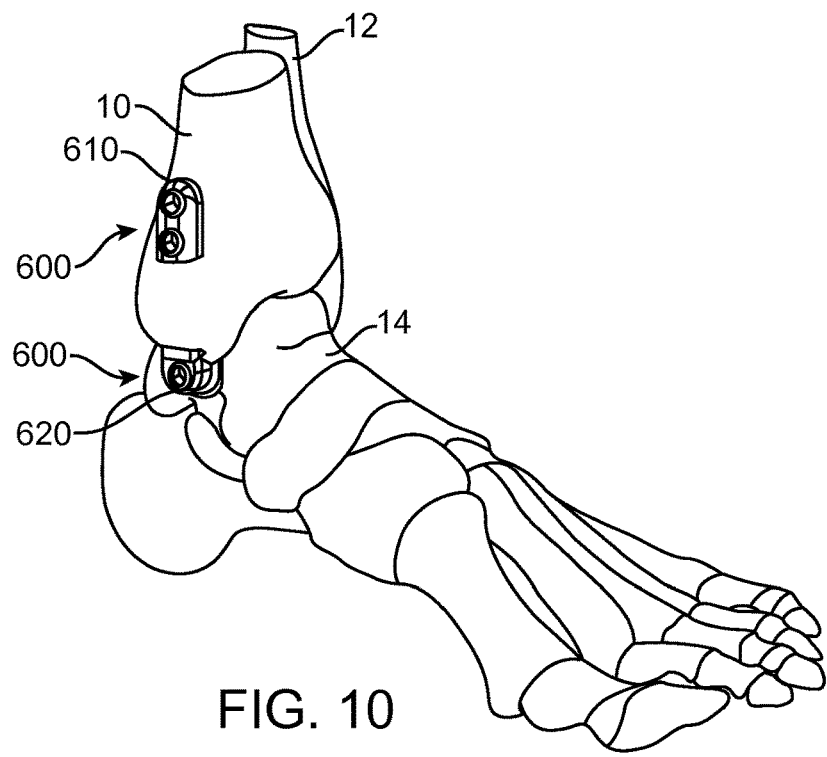
FIG. 10 is a medial side perspective view of an ankle having an implantable load absorbing device implanted.
Figure 11:
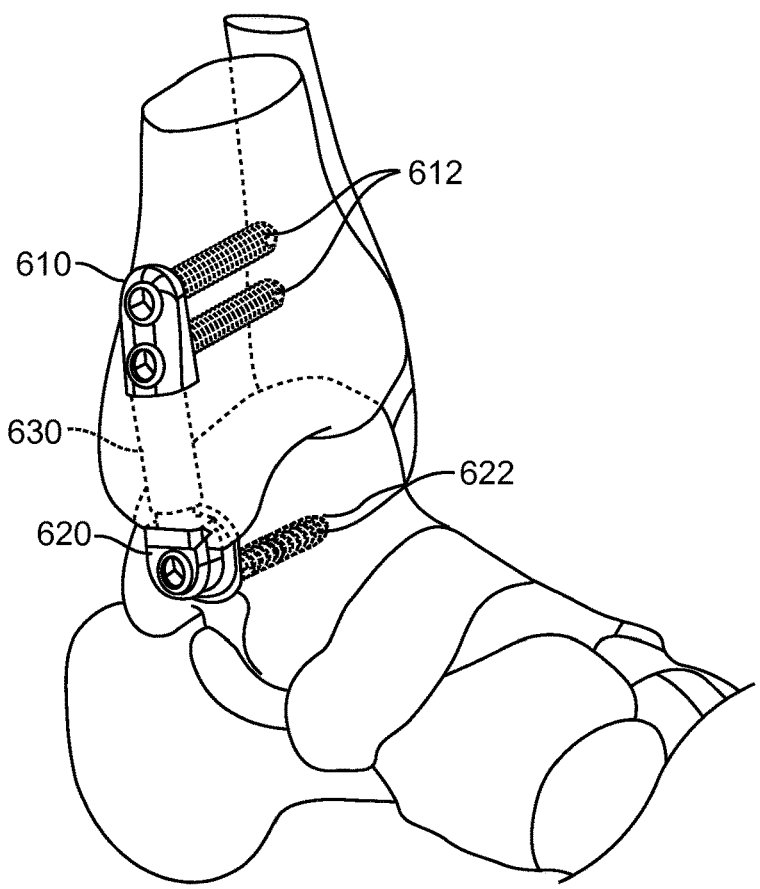
FIG. 11 is an enlarged medial side perspective view of the device of FIG. 10.

As shown in FIGS. 10 and 11, the absorber 630 extends through a tunnel in the medial malleolus of the tibia. This location of the absorber allows the profile of the device to be reduced without any significant impingement on the articular surfaces of the ankle. However, it should be understood that the absorber may also be positioned exterior to the bone while taking care to avoid the surrounding ligaments, tendons and other structures of the ankle.

Figure 12:
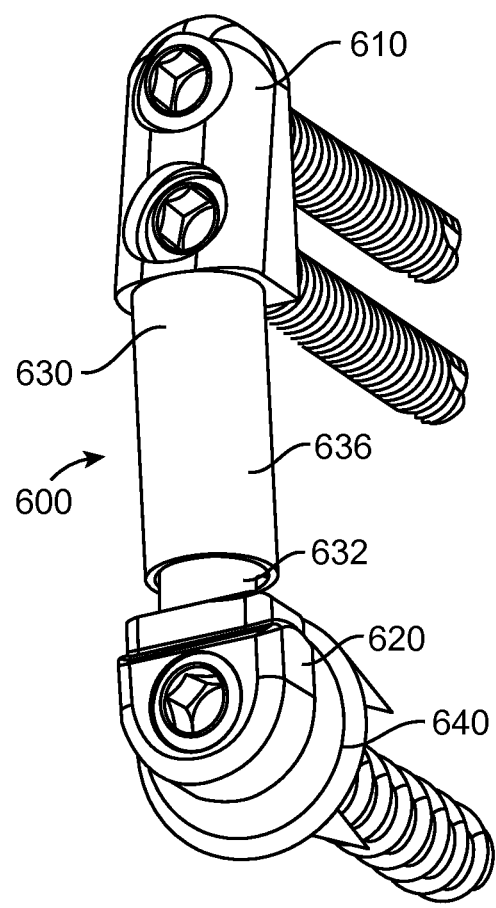
FIG. 12 is a perspective view of the device of FIG. 10.

The absorber 630 includes a central piston 632 (FIG. 13) surrounded by a coaxial compression spring 634 (FIG. 14) and covered by a sleeve 636 (FIG. 12). The sleeve 636 extends from and is formed integrally with the tibial load transmission support 610. Together the sleeve 636 and the piston 632 provide a telescoping arrangement. A length between the tibial and talus load transmission supports 610, 620 can change as the ankle joint articulates. This length change is accommodated by the telescoping arrangement of the absorber 630 which provides one degree of translational freedom as well as one degree of rotational freedom. The spring 634 may be connected on one end or may be entirely free floating such that no force is applied by the spring when the telescoping arrangement is in an extended position and a force is applied as the telescoping arrangement is compressed.

A second degree of translational freedom is provided by the talus load transmission support 620 which is slidable on the head of the talus screw 622 (FIG. 13). The sliding connection between the talus screw 622 and the talus support 620 also allows for rotation.

An additional degree of rotational freedom and an additional degree of translational freedom are provided by a joint between the piston 634 and the talus support 620. This saddle type joint allows the piston to translate slightly in an anterior/posterior direction and allows the piston to rotate slightly, such as during inversion/eversion of the ankle joint. Thus, this design has a total of three rotational degrees of freedom and three translational degrees of freedom to accommodate as nearly as possible full range of motion of the ankle joint while using a coil spring located within the medial malleolus to absorb at least a portion of a compressive load normally experienced by the natural ankle joint.

A washer 640, shown in FIG. 15, is positioned between the talus support 620 and the talus 14 to spread the forces over a larger area of the talus and to serve as a bearing surface for rotation of the talus support. The washer 640 is shown with a plurality of teeth for engaging bone and is not anatomy specific, however, other washer configurations could also be used. The washer can alternatively be formed as a part of the talus support 620 or can be provided in differing sizes, shapes and/or contours to accommodate patient differences.

Although the load absorbing device 600 of FIGS. 10-15 is illustrated only on the medial side of the ankle it should be understood that any of the load absorbing devices described herein can be applied at the medial and/or lateral sides of the ankle joint. When the load absorbing device 600 is implanted at both sides of the ankle joint, the device can include a rod configured to extend through the talus to secure the talus supports in place. This rod can extend through the talus substantially at a location of a center of rotation of the ankle joint or slightly anterior, posterior, inferior or superior to the center of rotation connecting the talus supports intraosseously depending on the load absorption profile desired.

The positioning of the tibial and talus supports 610, 620 can be arranged to cause compressive load absorption to change as the ankle joint articulates. For example, the load absorption can be at a maximum between ±5 degrees of flexion and can be at a minimum or at zero beyond some larger degree of flexion, such as ±15 degrees. In another example, load absorption can be active throughout the entire range of motion of the typical gait cycle.

Although the load absorbing device is active in applying a load bypassing force during only a portion of the range of motion of the joint, the device should arranged to permit a full range of motion abet during a portion of this range of motion the device is in a passive or inactive state. In one example, the implantable device 600 permits a full natural range of motion including 50° of motion in plantarflexion, 20° of motion in dorsiflexion, 20° range of motion in abduction, 35° of motion in adduction, 25° in internal and external rotation.

In various approaches to the ankle joint, the load absorbing devices can be attached at fixation points which allow the device to reside beneath or above the surrounding tendons, ligaments and muscles. In some cases, a portion of some of these structures, such as the deltoid ligament, may need to be displaced or resected to gain sufficient access to the ankle joint to effect a proper fixation.

The load transmission supports described herein can be specifically shaped or contoured to overlay mounting sites of the ankle bones and can be provided in a number of different sizes and shapes to accommodate differing patient anatomies.

To implant the load absorbing devices of the present invention, conventional surgical or minimally invasive approaches can be taken to gain access to a body joint or other anatomy requiring attention. Arthroscopic approaches are contemplated when reasonable to both implant the devices as well as to accomplish adjusting an implanted assembly. Biologically inert materials of various kinds can be employed in constructing the devices of the present invention. The materials can include titanium or titanium alloy, cobalt chromium alloy, ceramic, high strength plastic such as polyetheretherketone (PEEK) or other durable materials. Combinations of materials can also be used to maximize the properties of materials for different parts of the device. At the wear surfaces, the material may include a combination of metal-on-poly, metal-on-metal, metal-on-ceramic or other combinations to minimize wear.

In a related approach an absorber element can be embodied in an elastomeric absorber element which stiffens in compression and is capable of both elongation and bending. In one embodiment, the absorber element can be comprised of silicone, silicone ePTFE, or other elastomeric materials which permit lengthening but resist compression beyond a given amount. Soft and hard segments can be disbursed along the elastomeric absorber to provide the desired compression and lengthening.

The load absorbing devices described herein can be completely removable by a subsequent surgical procedure. Because the devices do not require resection or only require very minimal resection of the articulating surfaces of the ankle joint, and little or no ligaments or cartilage is removed the ability to perform a future procedure, such as an ankle replacement procedure is not effected. The procedure can be performed with only one or two short incisions at the ankle joint providing a less invasive procedure and a shorter recovery than ankle replacement surgery.

In using the load absorbing devices for ankles described herein, the physician determines whether to implant a load absorbing device and how much to unload the ankle based on certain characteristics of the patient injury or disease as will be described in detail below.

There has been postulated a relationship between elevated contact stress and the development of PTOA in the ankle. Thus, efforts to reduce elevated contact stresses within an ankle, for example, may minimize the risk of developing PTOA. Further, a physician can make a treatment decision about whether the load absorbing devices should be used for a particular patient based on estimates of contact stresses in the ankle.

By employing finite element analysis, contact stresses within joints can be estimated. For instance, cumulative stress exposures over a tibial articulating surface can be calculated and expressed in MPa-s, by summing the difference, over time, of finite element-computed nodal contact stress values at given increments in the gait cycle and a scalar contact stress damage threshold. The scalar contact stress damage threshold can be set at 6 MPa to be empirically consistent with minimal overexposure in intact ankles. Alternatively, in instances of unilateral disease or damage, the patients non diseased ankle may be analyzed and used as a baseline for overexposure.

Of the various contact stresses within an ankle which may be considered, the peak cumulative contact stress-time dose acting on an articular surface (expressed in MPa-s/gait cycle) can be deemed to be highly predictive of PTOA. Notably, this approach accounts for the effects of exposure time and area of engagement. Moreover, using this approach leads to the identification of a difference between ankle joints who later progressed to OA and ankles where there is no appreciable OA. In fact, the threshold above which patients having an ankle fracture progressed to OA was found to be about 30 MPa-s/gait cycle. Below this threshold, the ankle fracture healed with no or only mild PTOA resulting at 2 years post injury. Above this threshold patients experienced higher contact stress and had developed moderate to severe PTOA. Accordingly, in those patients having contact stress above about 30 MPa-s/gait cycle a load absorbing device according to the present invention would be suggested. The load absorbing device can either be permanently or temporarily implanted. The use of the device may be to treat a joint that has diagnosed OA disease or if used at the time of ankle fracture to prevent the onset of disease by allowing the ankle to heal without contact stresses above the threshold. The load absorbing device can either be permanently or temporarily implanted. If temporary, the time period for temporary use may depend on a combination of joint status, patient demographics and device load absorption and may range from about 4 weeks in some instances to a period of about 6 months to 2 years.

In determining the amount of unloading to provide, the difference in contact stresses between the patients progressing to PTOA and those experiencing mild or no PTOA was considered. The difference between mean peak cumulative time dose contact stresses for OA and no OA patients can generally be characterized to be in the range of 1.3 MPa-s. Thus, reducing the stress time dose in the ankle by 1.3 MPa-s may reduce pain in certain patients.

In order to reduce a stress time dose by 1.3 MPa-s, a certain load reduction across the ankle would be necessary. Assuming a reasonable walking cadence of 50 strides/min or a cycle every 0.83 seconds and 60% of the gait cycle being stance, leads to a load bearing time interval of approximately 0.5 seconds per gait cycle. Thus, to reduce stress dose by 1.3 MPa-s where there is a stance time interval of 0.5 seconds, it is contemplated that a 0.65 MPa reduction in pressure per gait cycle would be necessary to reduce pain in a typical patient.

It has also been observed that ankle contact areas can generally be in the range between 270 mm$^2$ and 415 mm$^2$. Ankles which have suffered trauma, such as intra-articular fractures, however, have associated therewith reduced contact areas post trauma. Assuming joint forces of approximately three times body weight, contact areas of post trauma ankles can be calculated.

Further, assuming joint forces of three times body weight and assessing an average body weight of 92.7 Kg, ankle joint contact areas can be approximated based on known peak stresses. Accordingly, to reduce contact stress by 0.65 MPa in an ankle joint, a target force reduction would be approximately 30 pounds. Thus, for the general population, it is expected that a force reduction of approximately 20-40 pounds could be effective in the reduction of pain across an ankle joint. A 30 pound reduction in force would work well for one size fits all load absorbing device designed to fit a majority of patients. Alternatively, a modular system can be provided with different springs available for fitting a patient based on the finite element stress analysis of the patient's particular joint. With finite element stress analysis, a difference between the estimated contact stress for the patient's joint can be compared to the predetermined threshold and a spring selected to reduce contact stress to a value at or below the threshold.

Thus, it will be apparent from the foregoing that, while particular forms of the invention have been illustrated and described, various modifications can be made without parting from the spirit and scope of the invention.

We claim:

1. An implantable load absorbing device for reducing ankle pain, the device comprising:
   a first load transmission support configured to conform to and to be non-pivotably secured to a medial side of a tibia;
   a second load transmission support configured to conform to and to be secured to a medial side of a talus; and
   an implantable compressible absorber defining an axis, the absorber being secured to the first support so that the absorber is non-pivotable about axes perpendicular to said absorber axis, said absorber being pivotably secured to the second support;
   wherein said second load transmission support and said absorber include a sliding joint configured to permit the absorber to translate linearly along said absorber axis;
   wherein the absorber is configured to off-load at least a portion of a compressive load normally experienced by a natural ankle joint; and
   wherein the absorber is configured such that no force is applied between the first and second supports beyond a point at which the absorber is in a first, extended configuration and a force is applied between the first and second supports when the absorber is in a second, compressed configuration.

2. The device of claim 1, wherein a length between the first and second load transmission supports changes as the ankle joint articulates.

3. The device of claim 1, wherein the second support includes at least one rod configured to extend through the talus substantially at a location of a center of rotation of the ankle joint.

4. The device of claim 1, further comprising an implantable lateral absorber secured to a third load transmission support and a fourth load transmission support configured to be secured to a lateral side of the talus.

5. The device of claim 4, wherein the third support is configured to be secured to a lateral side of the tibia anterior of the fibula.

6. The device of claim 4, wherein the third support is configured to be secured to a lateral side of the fibula.

7. The device of claim 4, wherein the second support and the fourth support are connected by at least one rod configured to extend through the talus substantially at a location of a center of rotation of the ankle joint.

8. The device of claim 1, wherein the implantable absorber is configured to extend at least partially through a medial malleolus of the tibia.

9. The device of claim 1, wherein the absorber includes at least one spring configured to absorb the compressive load.

10. The device of claim 9, wherein the at least one spring is configured to be at least partially located within a medial malleolus of the tibia.

11. The device of claim 1, wherein the absorber is secured to the second support by a connection having at least one degree of rotational freedom.

12. The device of claim 11, wherein the connection between the second support and the absorber has at least one degree of freedom in translation.

13. The device of claim 1, wherein the device is configured to be located entirely extra-articularly.

14. The device of claim 1, wherein at least one of the first and second supports comprises a single bone screw.

15. The device of claim 1, wherein the first and second supports are each secured in place with a plurality of bone screws.

16. An implantable device for reducing ankle pain, the device comprising:
   a first load transmission support configured to be non-pivotably secured to a tibia or fibula;
   a second load transmission support configured to be secured to a talus;
   an implantable absorber defining a longitudinal axis, the absorber being positioned between the first support and the second support and having at least a first degree of rotational freedom of motion about the second load transmission support, rotational freedom of motion only about said longitudinal axis of the absorber relative to the first load transmission support, a first degree of translational freedom of movement between the first support and the second support to allow ankle motion, and a sliding joint between the absorber and the second load transmission support which permits a second degree of translational movement between the second load transmission support and the absorber to permit the absorber to translate linearly along said absorber longitudinal axis while absorbing at least a portion of a compressive load normally experienced by a natural ankle joint; and
   wherein the absorber is configured such that no force is applied between the first and second supports beyond a point at which the absorber is in a first, extended configuration and a force is applied between the first and second supports when the absorber is in a second, compressed configuration.

17. The device of claim 16, wherein the device is configured to be implanted outside of the ankle joint.

18. An implantable device for reducing ankle pain, the device comprising:
   a first load transmission support configured to be non-pivotably secured to a tibia or fibula;
   a second load transmission support configured to be secured to a talus such that the second support is in contact with the first support during a portion of the natural motion of an ankle joint;
   at least one spring element in the first or second support configured to absorb at least a portion of a compressive load normally experienced by a natural ankle joint;
   wherein there is one degree of rotational freedom of motion about the second load transmission support, rotational freedom of motion only about a longitudinal axis of the at least one spring element relative to the first load transmission support, a first degree of translational freedom of motion movement between the first and second load transmission supports, and a sliding joint between the at least one spring element and the second load transmission support which permits a second degree of translational freedom of motion between the second load transmission support and the at least one spring element to permit the at least one spring element to translate linearly along said at least one spring element longitudinal axis; and
   wherein the absorber is configured such that no force is applied between the first and second supports beyond a point at which the absorber is in a first, extended configuration and a force is applied between the first and second supports when the absorber is in a second, compressed configuration.

19. An implantable load absorbing device for reducing ankle pain, the device comprising:
   a first load transmission support configured to conform to and to be secured to a medial side of a tibia;

a second load transmission support configured to be pivotably secured to a medial side of a talus;

an implantable compressible absorber non-pivotably secured to the first support and pivotably secured to the second support, the absorber defining a longitudinal axis;

wherein the absorber is configured to off-load at least a portion of a compressive load normally experienced by a natural ankle joint;

wherein the implantable absorber is configured to extend at least partially through a medial malleolus of the tibia;

wherein said second load transmission support and said absorber include a sliding joint configured to permit the absorber to translate linearly along said absorber longitudinal axis; and wherein the absorber is configured such that no force is applied between the first and second supports beyond a point at which the absorber is in a first, extended configuration and a force is applied between the first and second supports when the absorber is in a second, compressed configuration.

* * * * *